(12) United States Patent
Armengol Asparo et al.

(10) Patent No.: US 7,279,581 B2
(45) Date of Patent: Oct. 9, 2007

(54) PROCESS FOR PREPARING A PHARMACEUTICALLY ACTIVE COMPOUND

(75) Inventors: Montserrat Armengol Asparo, Sant Joan Despi (ES); Pere Dalmases Barjoan, Sant Feliu De Llobregat (ES)

(73) Assignee: Inke, S.A., Barcelona (ES)

( * ) Notice: Subject to any disclaimer, the term of this patent is extended or adjusted under 35 U.S.C. 154(b) by 547 days.

(21) Appl. No.: 10/509,918

(22) PCT Filed: Aug. 5, 2003

(86) PCT No.: PCT/IB03/03540

§ 371 (c)(1),
(2), (4) Date: Oct. 4, 2004

(87) PCT Pub. No.: WO2004/014877

PCT Pub. Date: Feb. 19, 2004

(65) Prior Publication Data

US 2005/0148778 A1    Jul. 7, 2005

(30) Foreign Application Priority Data

Aug. 7, 2002    (ES)    ............... 200201874

(51) Int. Cl.
*C07D 249/08*    (2006.01)
(52) U.S. Cl. .................. 548/266.4; 548/262.2
(58) Field of Classification Search ............. 548/262.2, 548/266.4
See application file for complete search history.

(56) References Cited

U.S. PATENT DOCUMENTS 5,567,824 A * 10/1996 Chen et al. ................. 548/252

FOREIGN PATENT DOCUMENTS

| EP | 0497512 | 8/1992 |
|---|---|---|
| ES | 2033577 | 3/1993 |
| ES | 2033578 | 3/1993 |
| WO | 9402476 | 2/1994 |
| WO | 9532197 | 11/1995 |
| WO | 9806725 | 2/1998 |
| WO | 0134561 | 5/2001 |

* cited by examiner

*Primary Examiner*—Golam M. M. Shameem
(74) *Attorney, Agent, or Firm*—Wolf Block Schorr & Solis-Cohen LLP

(57) ABSTRACT

In particular, rizatriptan or a pharmaceutically acceptable salt thereof, which includes a) Preparation of the diazonium salt of aniline hydrochloride (II); followed by reduction and acidification to give the hydrazine (III); b) reaction in situ of the hydrazine hydrochloride (III) with α-keto-δ-valerolactone, to give the hydrazone (IV); c) Fischer indole reaction of the hydrazone (IV), to give the pyranoindolone (V), optionally followed by a hydrolysis reaction to give (VI); d) Transesterification of (V) or esterification of its hydrolysis product (VI), to give (VII), where R means straight or branched C1-C4 alkyl chain; e) Conversion of the hydroxyl group of (VII) into dimethylamino, to give the indolecarboxylate (VIII), where R has the meaning defined above; f) Saponification of the 2-carboalkoxy group of (VIII) to give indolecarboxylic acid (IX); and g) Decarboxylaton of the indolecarboxylic acid (IX) to give rizatriptan and, eventually, to obtain a pharmaceutically acceptable salt thereof. The invention also relates to synthesis intermediates to obtain rizatriptan.

13 Claims, No Drawings

PROCESS FOR PREPARING A PHARMACEUTICALLY ACTIVE COMPOUND

FIELD OF THE INVENTION

This invention relates to a new process for preparing a pharmaceutically active compound. In particular, it relates to a process for preparing rizatriptan.

BACKGROUND OF THE INVENTION

Patent EP 497512 describes derivatives of imidazole, triazole and tetrazole which act on the 5-HT receptor. Notable among them is the compound 3-[2-(dimethylamino) ethyl]-5-(1,2,4-triazol-1-ylmethyl)-indole, of formula (I):

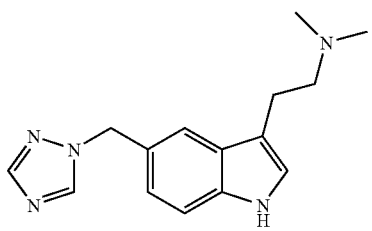

This compound is known by the INN rizatriptan and is marketed as an anti-migraine product.

The aforesaid European patent describes the preparation of rizatriptan by Fischer indole synthesis, using the corresponding phenylhydrazine and an aldehyde. The method described in that patent nevertheless has the following disadvantages: it requires several steps of column purification and has an overall yield of only 11%.

Other processes for preparing rizatriptan were described subsequently.

On the one hand, preparation of the intermediate (4-[1,2,4]triazol-1-1-ylmethyl-phenyl)-hydrazine is optimised by International Patent Application WO 94/02476. Conversion of this intermediate into rizatriptan is carried out by Fisher indole synthesis, in the same way as in the preceding patent. The yield for obtaining intermediate is improved by said process. The end product nevertheless continues to have the disadvantage of requiring a column purification step, so that it is not cost-effective to carry out the process at industrial scale.

As well, International application WO 95/32197 describes a process for preparing the product sought, by palladium-catalysed coupling ring closure of 3-iodine-4-aminobenzyl-triazol with a suitably protected butynol derivative to the corresponding tryptophol followed by conversion of the hydroxyethyl moiety to dimethylaminoethyl. Although this process does not require column purification, it has the disadvantage of using a palladium catalyst which makes the process more expensive, while also using highly toxic reagents such as iodine chloride and highly flammable ones such as n-butyl lithium.

Finally, application WO 98/06725 describes the preparation of 2-silyl protected indoles, by palladium-catalysed cross-coupling reaction of haloanilines with acylsilanes, and preparation of the product sought by deprotection of these intermediates so obtained. This process also has the disadvantage of using a palladium catalyst which makes the process more expensive, while it also uses highly flammable reagents such as n-butyl lithium.

DESCRIPTION OF THE INVENTION

A first aspect of this invention is to provide a new process for preparing rizatriptan or a pharmaceutically acceptable salt thereof, which includes the following steps:

a) Preparation of the diazonium salt of the aniline hydrochloride of formula (II)

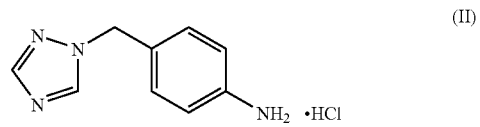

followed by reduction and acidification to give the hydrazine of formula (III):

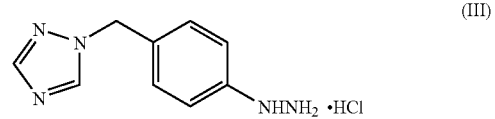

b) In situ reaction of the hydrazine hydrochloride of formula (III) with α-keto-δ-valerolactone to give the hydrazone of formula (IV):

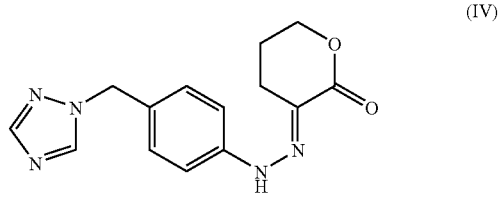

c) Fischer indole synthesis of the hydrazone of formula (IV) to give the pyranoindolone of formula (V):

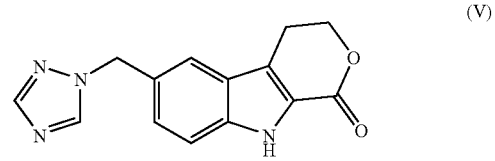

optionally, followed by a hydrolysis reaction to provide the product of formula (VI):

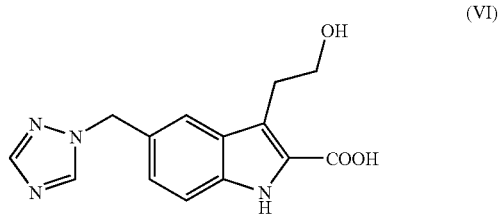

d) Transesterification of the compound of formula (V) or esterification of its hydrolysis product of formula (VI), to provide a compound of formula (VII):

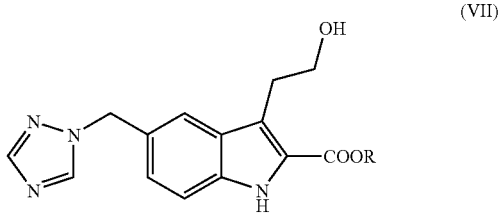

in which R represents a straight or branched C1-C4 alkyl chain;

e) Conversion of the hydroxyl group of the compound of formula (VII) into dimethylamino, to give the indolecarboxylate of formula (VIII):

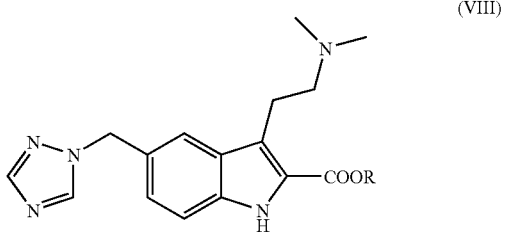

in which R has the same meaning defined above;

f) Saponification of the 2-carboalkoxy group of the compound of formula (VIII), to provide the indolecarboxylic acid of formula (IX):

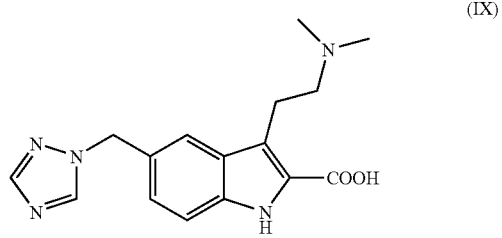

g) Decarboxylation of the indolecarboxylic acid of formula (IX), to provide rizatriptan and, eventually, the preparation of a pharmaceutically acceptable salt thereof.

The process for preparing rizatriptan object of this invention has the advantages compared with the prior art of not requiring expensive catalysts or highly toxic or highly flammable reagents, as well as involving no steps of column purification, which makes it a process suitable for carrying out at industrial scale.

Following, each of the steps of the general process for preparing rizatriptan will be described in more detail.

Preparation of the diazonium salt of the aniline hydrochloride of formula (II) is carried out by treating this compound with sodium nitrite and hydrochloric acid at low temperature. Subsequent reduction thereof is effected with an alkaline metal sulphite followed by acidification to give the hydrazine of formula (III).

Reaction of the hydrazine hydrochloride of formula (III) with α-ketovalerolactone is carried out in aqueous medium at a temperature between 10° C. and 100° C., at a pH between 0.1 and 4, preferably at pH=1.

Steps a), b) and c) are preferably carried out as a "one pot" reaction, that is, without isolating the intermediates. In this case the indolisation reaction of the hydrazone of formula (IV) is carried out in the solution resulting from step b), i.e. in aqueous medium, at a pH between 0.1 and 4, and at a temperature between 40° C. and 100° C., preferably between 70° C.-80° C., and the hydrolysis reaction is then carried out in situ by addition of alkaline hydroxide, preferably aqueous sodium hydroxide, to give the compound of formula (VI), which is separated by conventional methods.

Alternatively, after steps a) and b) the compound of formula (IV) can be isolated by conventional methods. In this case Fischer indole synthesis of the hydrazone of formula (IV) is carried out under conditions similar to those described in patent GB 1189064 for preparing carboalkoxy-indoles. It is thus preferably carried out in a solution of dry hydrogen chloride in acetic acid or in a C1-C4 alcohol (such as methanol, ethanol, etc.). The reaction can be carried out at a temperature between 0° C. and 80° C., preferably at room temperature. Following the indolisation reaction the pyranoindolone of formula (V) can be isolated by conventional methods.

The transesterification or esterification reaction of step d) can then be carried out in an alcoholic solution, preferably methanol, and in the presence of an acid, preferably methanesulphonic acid. The product is isolated by conventional methods.

Conversion of the hydroxyl group of the compound of formula (VII) into a dimethylamino group is carried out preferably by substituting the hydroxyl group by a leaving group X and subsequent substitution reaction of the leaving group X with dimethylamine. Preferably, X is a halogen atom, a mesylate group (OMs) or a tosylate group (OTs).

The substitution of the hydroxyl group of the compound of formula (VII) by a leaving group X can be carried out by reacting it with mesyl chloride or tosyl chloride or by replacing said hydroxyl by a halogen, using conventional halogenation reagents. When X=OTs, the reaction is carried out in a suitable solvent, such as toluene, in the presence of pyridine and using 4-(dimethylamino)pyridine as catalyst. When X=OMs, the reaction is carried out in a suitable solvent, such as tetrahydrofuran, in the presence of triethylamine as catalyst. The reaction can be carried out at a temperature between 0° C. and 50° C., preferably at room temperature. The product is isolated by conventional methods.

In the case of the tosylates, the substitution reaction of the leaving group X with dimethylamine takes place under particularly gentle conditions. This reaction is carried out in an alcoholic solution or in an aqueous solution, at a temperature between 0° C. and 100° C., preferably between 40° C. and 80° C. The product is isolated by conventional methods.

The saponification of the 2-carboalkoxy group of the compound of formula (VIII) is carried out in alkaline medium, preferably in an alcoholic solution of potassium hydroxide, and at a temperature between 20° C. and 100° C., preferably at reflux temperature. The product is isolated by conventional methods.

The decarboxylation of the indolecarboxylic acid of formula (IX) is carried out in the presence of an inert solvent of high boiling point and a suitable catalyst, in an inert atmosphere and at a temperature between 180° C. and 250° C. Preferably, the solvent is quinoline or a mixture of quinoline and an organic solvent such as triethylene glycol dimethyl ether, diphenyl ether, etc. Catalysts can be chosen from powdered copper, cuprous oxide, cuprous chloride, cupric chromite, copper pentafluorophenyl or the cupric salt of the compound of formula (IX) used in a molar proportion between 5% and 10% in relation to the compound of formula (IX). The inert atmosphere can be created by dry nitrogen stream. The reaction is preferably carried out at 200° C. The product is isolated by conventional methods.

The initial products can be obtained as indicated below.

The aniline hydrochloride of formula (II) can be obtained by reduction of the corresponding nitro derivative, as described in European patent EP 497512.

α-keto-δ-valerolactone can be obtained by decarboxylation of α-ethoxalyl-γ-butirolactone in 2N $H_2SO_4$ at reflux.

A second aspect of the present invention is the synthesis intermediate of formula (IV):

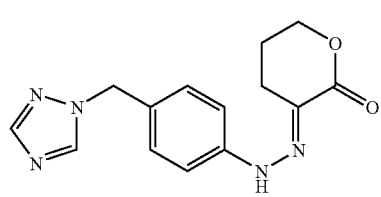

(IV)

A third aspect of the present invention is the synthesis intermediate of formula (V):

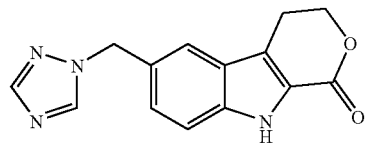

(V)

A fourth aspect of the present invention is the synthesis intermediate of formula (VI):

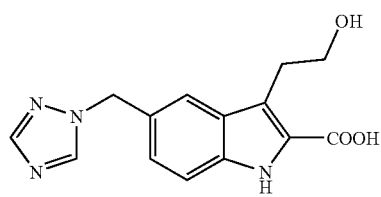

(VI)

A fifth aspect of the present invention is a synthesis intermediate of formula (VII):

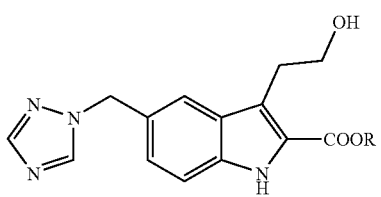

(VII)

in which R represents a straight or branched C1-C4 alkyl chain.

A sixth aspect of the present invention is a synthesis intermediate of formula (VIII):

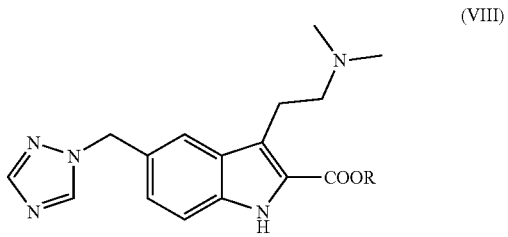

(VIII)

in which R represents a straight or branched C1-C4 alkyl chain.

A seventh aspect of the present invention is the synthesis intermediate of formula (IX):

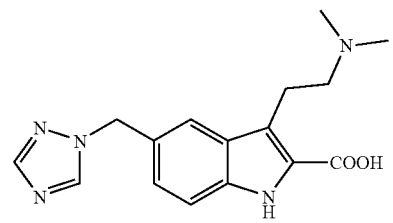

(IX)

The aforesaid synthesis intermediates of formula (IV), (V), (VI), (VII), (VIII) and (IX) are useful for the synthesis of rizatriptan, although their use for synthesis of other products likewise forms part of the scope of protection of this invention.

The steps described above in the general process for providing rizatriptan can therefore be considered independent processes for preparing the intermediate synthesis products, isolating the intermediate product where necessary.

There follows a description of the steps of the general process as independent procedures for preparing the synthesis intermediates.

A first process relates to preparation of the intermediate of formula (IV) by reaction of the hydrazine hydrochloride of formula (III) with α-keto-δ-valerolactone, in accordance with step b) of the first aspect of the invention.

A second process relates to preparation of the intermediate of formula (V) by Fischer indole synthesis of the hydrazone of formula (IV), in accordance with step c) of the first aspect of the invention.

A third process relates to preparation of the intermediate of formula (VI) by Fischer indole synthesis of the hydrazone of formula (IV) followed by the step of hydrolysis, in accordance with step c) of the first aspect of the invention.

a fourth process relates to preparation of the intermediate of formula (VII) by transesterification of the compound of formula (V) or esterification of its hydrolysis product of formula (VI), in accordance with step d) of the first aspect of the invention.

A fifth process relates to preparation of the intermediate of formula (VIII) by conversion of the hydroxyl group of the intermediate of formula (VII) in dimethylamine, in accordance with step e) of the first aspect of the invention.

A sixth process relates to preparation of the intermediate of formula (IX) by saponification of the 2-carboalkoxy group of the intermediate of formula (VIII), in accordance with step f) of the first aspect of the invention.

Outlined below by way of explanation are the following non-restrictive examples of the invention.

EXPERIMENTAL PART

EXAMPLES OF SYNTHESIS

Example 1

3-(2-Hydroxyethyl)-5-[1,2,4]triazol-1-ylmethyl-1H-indol-2-carboxylic acid

To a solution of 3 g (14.28 mmoles) of 4-(1,2,4-triazol-1-ylmethyl)phenylamine hydrochloride in 6 ml of water and 11.5 ml of concentrated HCl, cooled to 0° C., a solution of 1 g (14.5 mmoles) of sodium nitrite in 2 ml of water was added slowly, keeping the temperature below 0° C. The mixture was stirred at this temperature for 15 minutes. The diazonium salt solution was then added rapidly to a solution of 10.8 g (85.7 mmoles) of sodium sulphite in 21.5 ml of water precooled to 0° C. under nitrogen atmosphere. The red solution was stirred at 0° C. for 10 minutes and then left to reach 65° C. in 1 hour. It was stirred at 65° C. for 30 minutes, and 6 ml of concentrated HCl then added. The mixture was stirred at the same temperature under nitrogen atmosphere for 1 hour and then left to cool to room temperature. To this solution was added a solution of 22.8 mmoles of α-keto-δ-valerolactone(prepared by decarboxylation of 2.1 g (11.4 mmoles) of α-ethoxalyl-γ-butirolactone in 6.6 ml of 2N $H_2SO_4$ at reflux) and left under stirring at 70° C. for 7 hours. When that time had elapsed the mixture was cooled to 40° C. and added to 17 ml of 20% NaOH aqueous solution and 6 ml of ethanol. The mixture was washed with (15×2 ml) of AcOEt. The aqueous phase was filtered through decalite and adjusted to pH 4 with 2.5 ml of concentrated HCl. The yellow solid precipitated was filtered, washed with cold water and dried in a hot-air oven at 40° C. to constant weight, giving 3.5 g (85%) of the title hydroxy acid as a yellow solid.

IR (KBr): 1133, 1238, 1511, 1555, 1672, 3278, 3535 cm$^{-1}$.

$^1$H-NMR (200 MHz, DMSO-d$_6$): 3.21 (t, J=7.2 Hz, 2H, CH$_2$CH$_2$OH); 23.60 (t, J=7.2 Hz, 2H, CH$_2$CH$_2$OH); 5.45 (s, 2H, CH$_2$-benz.); 7.20 (dd, J=1.6 and 8.4 Hz, 1H, ar); 7.37 (d, J=8.4 Hz, 1H, ar); 7.68 (d, s, 1H, ar); 7.97 (s, 1H, tz); 8.65 (s, 1H, tz); 11.52 (s, 1H, NH-indole).

$^{13}$C-NMR (200 MHz, DMSO-d$_6$): 28.5; 53.1; 61.9; 112.8; 119.7; 120.5; 125.1; 125.3; 127.2; 127.8; 135.8; 144.0; 151.7; 163.5.

Example 2

3-(2-Hydroxyethyl)-5-(1,2,4-triazol-1-ylmethyl)-1H-indol-2-carboxylic acid methyl ester 2.7 ml (42 mmoles) of methanesulphonic acid were added to a suspension de 6 g (21 mmoles) of the 3-(2-hydroxyethyl)-5-[1,2,4]triazol-1-ylmethyl-1H-indol-2-carboxylic acid in 120 ml of methanol. The mixture was left under stirring at reflux temperature for 3 hours. The solvent was evaporated to dryness under reduced pressure, the residue dissolved with 20 ml of a saturated bicarbonate solution and extracted 3 times with ethyl acetate. The combined organic phases were dried and evaporated to dryness, and the evaporated solid recrystallised from isopropyl alcohol/heptane to give 5.9 g (93%) of the title ester as a yellow crystalline solid.

M.p. 177.8-179.5° C.

IR (KBr): 1704, 3230 cm$^{-1}$.

$^1$H-NMR (200 MHz, DMSO-d$_6$): 3.19 (m, 2H, CH$_2$CH$_2$OH); 3.58 (m, 2H, CH$_2$CH$_2$OH); 3.86 (s, 3H, CH$_3$); 4.71 (t, J=5.2 Hz, 1H, OH); 5.45 (s, 2H, CH$_2$-benz.); 7.22 (d, J=8, 4 Hz, 1H, ar); 7.37 (d, J=8.4 Hz, 1H, ar); 7.68 (s, 1H, ar); 7.95 (s, 1H, tz); 8.64 (s, 1H, tz); 11.62 (s, 1H, NH-indole).

$^{13}$C-NMR (200 MHz, DMSO-d$_6$): 29.1; 52.3; 53.4; 62.3; 113.4; 121.1; 124.5; 126.0; 128.0; 128.2; 136.6; 144.6; 152.3; 162.7.

Example 3

3-[4-(1,2,4-Triazol-1-ylmethyl)phenyl-hidrazono]tetrahydropyran-2-one a. (4-[1,2,4]Triazol-1-ylmethylphenyl)hydrazine hydrochloride To a solution of 1.5 g (7.1 mmoles) of 4-(1,2,4-triazol-1-ylmethyl)phenylamine hydrochloride in 3.75 ml of water and 6.3 ml of concentrated HCl, cooled to 0° C., was added slowly a solution of 0.5 g (7.2 mmoles) of sodium nitrite in 2.6 ml of water, keeping the temperature below 0° C. The mixture was stirred at this temperature for 15 minutes. Once this time had elapsed the solution of the diazonium salt was added rapidly to a solution of 5.37 g (42.6 mmoles) of sodium sulphite in 19 ml of water precooled to 0° C. under nitrogen atmosphere. The red solution was stirred at 0° C. for 10 minutes and then left to reach 65° C. in 1 hour. It was stirred at 65° C. for 30 minutes, and 5 ml of concentrated HCl were then added. The mixture was stirred at the same temperature under nitrogen atmosphere for 3 hours and then left to cool to room temperature.

b. 3-[4-(1,2,4-Triazol-1-ylmethyl)phenylhidrazono]tetrahydropyran-2-one

To the solution obtained in the previous section is added a solution of 11.4 mmoles of α-keto-δ-valerolactone(prepared by decarboxylation of 2.1 g (11.4 mmoles) of α-ethoxalyl-γ-butirolactone in 3.15 ml of 2N $H_2SO_4$ at reflux) and left under stirring at room temperature for 12 hours. Once this time had elapsed the mixture was cooled to 0° C. and adjusted to pH 6 with a 20% NaOH solution, precipitating a yellow solid which was filtered, washed with water and dried in hot-air oven at 40° C., to give a yellow solid which was crystallised from ethanol/water to give 1.72 g (85%) of the title hydrazone as a yellow solid.

M.p. 213.6-215.0° C.

IR (KBr): 1122 cm$^{-1}$, 1244 cm$^{-1}$, 1505 cm$^{-1}$, 1550 cm$^{-1}$, 1705 cm$^{-1}$.

$^1$H-NMR (200 MHz, DMSO-d$_6$): 1.98 (m, 2H, γ-lactone); 2.59 (m, 2H, β-lactone); 4.27 (m, 2H, γ-lactone); 5.31 (s, 2H, CH$_2$-benz.); 7.25 (s, 4H, ar); 7.96 (s, 1H, tz); 8.61 (s, 1H, tz); 10.08 (s, 1H, NH-hydrazone).

$^{13}$C-NMR (200 MHz, DMSO-d$_6$): 21.3; 24.5; 52.0; 67.5; 114.2; 129.0; 129.2; 131.2; 144.1; 151.8; 162.2.

Example 4

6-(1,2,4-Triazol-1-ylmethyl)-4,9-dihydro-3H-pyrano [3,4-b]indol-1-one hydrochloride 1.7 g (5.9 mmoles) of 3-[4-(1,2,4-Triazol-1-ylmethyl) phenylhydrazono]tetrahydropyran-2-one were added to a stirred solution of 15 ml absolute ethanol saturated with dry hydrogen chloride. The stirring was continued at room temperature for 16 hours. 5 ml of water/ice were added to the reaction mixture, and the mixture then stirred at 0° C. for 20 min. The precipitate was filtered, washed with ethanol/water and dried in hot-air oven at 40° C., to give 1.65 g (92%) of the title compound as a white solid.

M.p. 231.1-233.8° C.

IR (KBr): 1705 cm$^{-1}$.

$^1$H-NMR (200 MHz, DMSO-d$_6$): 3.09 (t, J=6.0 Hz, 2H, γ-lactone); 4.61 (t, J=6.0 Hz, 2H, δ-lactone); 5.51 (S, 2H, CH$_2$-benz.), 7.32 (d, J=8.6 Hz, 1H, ar); 7.43 (d, J=8.6 Hz, 1H, ar); 7.70 (s, 1H, ar); 8.21 (s, 1H, tz); 9.00 (s, 1H, tz); 12.04 (s, 1H, NH-indole).

$^{13}$C-NMR (200 MHz, DMSO-d$_6$): 21.5; 53.8; 69.9; 113.9; 121.8; 123.1; 123.7; 124.7; 127.1; 128.1; 138.5; 144.1; 151.0; 161.0.

Example 5

3-(2-Hydroxyethyl)-5-(1,2,4-triazol-1-ylmethyl)-1H-indol-2-carboxylic acid methyl ester To a suspension of 2.5 g (8.2 mmoles) of the 6-(1,2,4-triazol-1-ylmethyl)-4,9-dihydro-3H-pyrano[3,4-b]indol-1-on a hydrochloride in 50 ml of methanol were added 0.66 ml (10.2 mmoles) of methanesulphonic acid. The mixture was left under stirring at the reflux temperature for 4 hours. The solvent was evaporated to dryness under reduced pressure, the residue dissolved with 10 ml of a saturated bicarbonate solution and extracted 3 times with ethyl acetate. The combined organic phases were dried and evaporated to dryness and the evaporated solid recrystallised from isopropyl alcohol/heptane to give 2.3 g (94%) of the title ester as a yellow crystalline solid.

M.p. 177.8-179.5° C.

IR (KBr): 1704 cm$^{-1}$, 3230 cm$^{-1}$.

$^1$H-NMR (200 MHz, DMSO-d$_6$): 3.19 (m, 2H, CH$_2$CH$_2$OH); 3.58 (m, 2H, CH$_2$CH$_2$OH); 3.86 (s, 3H, CH$_3$); 4.71 (t, J=5.2 Hz, 1H, OH); 5.45 (s, 2H, CH$_2$-benz.); 7.22 (d, J=8.4 Hz, 1H, ar); 7.37 (d, J=8.4 Hz, 1H, ar); 7.68 (s, 1H, ar); 7.95 (s, 1H, tz); 8.64 (s, 1H, tz); 11.62 (s, 1H, NH-indole).

$^{13}$C-NMR (200 MHz, DMSO-d$_6$): 29.1; 52.3; 53.4; 62.3; 113.4; 121.1; 124.5; 126.0; 128.0; 128.2; 136.6; 144.6; 152.3; 162.7.

Example 6

3-[2-Toluen-4-sulphonyloxy)ethyl]-5-(1,2,4-triazol-1-ylmethyl)-1H-indol-2-carboxylic acid methyl ester To a stirred suspension of 1.3 g (4.3 mmoles) of 3-(2-hydroxyethyl)-5-(1,2,4-triazol-1-ylmethyl)-1H-indol-2-carboxylic acid methyl ester in 7.1 ml of dichloromethane were added 0.71 ml of pyridine, 1.3 g (6.9 mmoles) of tosyl chloride and 53 mg (0.43 mmoles) of dimethylaminepyridine and the stirring then continued at room temperature for 20 hours. The reaction mixture was then poured onto 5 ml of 3N HCl precooled to 0° C. and extracted three times with 20 ml of dichloromethane. The combined organic phases were then washed with brine, dried on anhydrous sodium sulphate and the solvent evaporated to dryness. The evaporated solid was crystallised from isopropyl alcohol to give 1.9 g (97%) of the title tosylate as a white solid.

IR (KBr): 1255 cm$^{-1}$, 1438 cm$^{-1}$, 1511 cm$^{-1}$, 1550 cm$^{-1}$, 1700 cm$^{-1}$.

$^1$H-NMR (200 MHz, DMSO-d$_6$): 2.34 (s, 3H, CH$_3$); 3.30 (t, J=6.4 Hz, 2H, CH$_2$CH$_2$Ots); 3.81 (s, 3H, OCH$_3$); 4.23 (t, J=6.4 Hz, 2H, CH$_2$CH$_2$Ots); 5.43 (s, 2H, CH$_2$-benz.); 7.23 (m, 3H, ar); 7.36 (d, J=8.4 Hz, 1H, ar); 7.45 (d, J=8.6 Hz, 2H, ar); 7.58 (s, 1H, ar); 8.00 (S, 1H, tz); 8.68 (s, 1H, tz); 11.74 (s, 1H, NH-indole).

$^{13}$C-NMR (200 MHz, DMSO-d$_6$): 14.3; 25.6; 44.7; 52.9; 60.6; 113.0; 118.9; 119.2; 120.4; 125.5; 125.6; 127.1; 127.2; 127.3; 127.8; 129.8; 135.9; 144.7; 161.5.

Example 7

3-(2-Dimethylaminoethyl)-5-[1,2,4-triazol-1ilmethyl]-1H-indol-2-carboxylic acid methyl ester 1.2 g (2.6 mmoles) of 3-[2-Toluen-4-sulphonyloxy) ethyl]-5-(1,2,4-triazol-1-ylmethyl)-1H-indol-2-carboxylic acid methyl ester were dissolved with 14 ml of a 2N dimethylamine solution in methanol. The solution was stirred at 50° C. for 20 hours in a closed reactor. The solvent was evaporated to dryness, the residue dissolved in 20 ml of 3N HCl and washed three times with 10 ml of dichloromethane. The washed aqueous phase was cooled and adjusted to pH 12 with a 40% sodium hydroxide solution and extracted three times with 20 ml of dichloromethane. The combined organic phases were washed with 20 ml of brine and dried on anhydrous sodium sulphate. The solvent was evaporated to dryness to give 800 mg (94%) of the title compound. The product was recrystallised from ethanol to give a white solid.

M.p. 151.7-153.0° C.

IR (KBr): 1694 cm$^{-1}$.

$^1$H-NMR (200 MHz, DMSO-d$_6$): 2.12 (S, 6H, N(CH$_3$)$_2$); 2.47 (m, 2H, CH$_2$CH$_2$N); 3.15 (t, J=7.6 Hz, 2H, CH$_2$CH$_2$N); 3.86 (s, 3H, OCH$_3$); 5.46 (s, 2H, CH$_2$-benz.); 7.20 (d, J=8.6 Hz, 2H, ar); 7.37 (d, J=8.6 Hz, 2H, ar); 7.64 (s, 1H, ar); 7.96 (s, 1H, tz); 8.65 (s, 1H, tz); 11.65 (s, 1H, NH-indole).

$^{13}$C-NMR (200 MHz, DMSO-d$_6$): 22.2; 44.9; 51.7; 52.8; 59.9; 112.9; 120.2; 121.4; 123.7; 125.4; 127.1; 127.5; 136.0; 144.0; 151.7; 162.0.

Example 8

3-(2-Hydroxyethyl)-5-[1,2,4-triazol-1-ylmethyl]-1H-indol-2-carboxylic acid

To a solution of 705 mg (12.6 mmoles) of KOH in 15 ml of ethanol was added 1.4 g (4.2 mmoles) of 3-(2-dimethylaminoethyl)-5-[1,2,4-triazol-lilmethyl]-1H-indol-2-carboxylic acid methyl ester, and the resulting solution stirred at reflux temperature for 1 hour. The solvent was cooled and evaporated to dryness. The residue was redissolved in 6 ml of water and washed three times with 10 ml of dichloromethane. The aqueous solution was cooled to 5° C. and adjusted to pH 6 with glacial acetic acid and stirred at this temperature for 30 minutes. The solvent was concentrated to one half, 15 ml of isopropyl alcohol added, the mixture stirred for 1 hour at 0° C. and the precipitated solid filtered and dried in hot-air oven at 40° C., to give 1.25 g (94%) of the title acid as a white crystalline solid.

M.p. 231.4° C. (dec.).

IR (KBr): 1594 cm$^{-1}$, 1361, 1333 cm$^{-1}$.

$^1$H-NMR (200 MHz, D$_2$O): 2.85 (s, 6H, N(CH$_3$)$_2$), 3.29 (s, 4H, CH$_2$CH$_2$N), 5.31 (s, 2H, CH$_2$), 7.23 (d, J=8.6 Hz, 1H, ar), 7.37 (d, J=8.6 Hz, 1H, ar), 7.46 (s, 1H, ar), 8.00 (s, 1H, tz), 8.42 (s, 1H, tz).

$^{13}$C-NMR (200 MHz, D$_2$O): 22.6; 46.0; 56.3; 61.5; 115.6; 115.7; 122.1; 127.2; 129.1; 129.9; 134.0; 137.5; 146.9; 154.1; 172.0.

Example 9

N,N-Dimethyl-2-[5-(1,2,4-triazol-1-ylmethyl)-1H-indol-3-il]ethylamine 700 mg (2,2 mmoles) of 3-(2-hydroxyethyl)-5-[1,2,4-triazol-1-ylmethyl]-1H-indol-2-carboxylic acid was suspended in 7 ml of dry quinoline. 14 mg of cuprous oxide was added and the stirred suspension heated, under dry nitrogen stream, to 200° C. The reaction mixture was kept at this temperature until no more CO$_2$ was released (15-20 min.). It was left to cool to room temperature and the reaction mixture was filtered through decalite. The filtrate was concentrated by vacuum distillation of the solvent, providing a residue which was dissolved with a succinic acid solution and washed three times with 10 ml of dichloromethane. The washed aqueous phase was cooled and adjusted to pH 12 with a 40% sodium hydroxide solution and extracted three times with 20 ml of dichloromethane. The combined organic phases were dried on anhydrous sodium sulphate and evaporated to dryness. The residue was recrystallised from heptane/isopropyl acetate to give 510 mg (86%) of rizatriptan as a white solid.

M.p. 120-122° C.

$^1$H-NMR (200 MHz, CDCl$_3$): 2.33 (s, 6H, N(CH$_3$)$_2$); 2.62 (t, J=8.2 Hz, 2H, CH$_2$CH$_2$N); 2.88 (t, J=8.2 Hz, 2H, CH$_2$CH$_2$N); 5.41 (s, 2H, CH$_2$-benz.); 7.06 (m, 2H, ar); 7.31 (d, J=8.4 Hz, 1H, ar); 7.55 (s, 1H, ar); 7.96 (s, 1H, tz); 7.99 (s, 1H, tz); 8.59 (ba, 1H, NH-indole).

$^{13}$C-NMR (200 MHz, CDCl$_3$): 23.5; 45.4; 54.5; 60.1; 111.8; 114.4; 119.2; 122.2; 122.6; 124.8; 127.7; 136.1; 142.7; 151.8.

Example 10

N,N-Dimethyl-2-[5-(1,2,4-triazol-1-ylmethyl)-1H-indol-3-il]ethylamine. Benzoate

A solution of 147 mg (1.2 mmoles) of benzoic acid in 1 ml of isopropyl acetate was added slowly to a solution of 300 mg (1.1 mmoles) of the rizatriptan base in 2.6 ml of isopropyl alcohol. The mixture was stirred at room temperature for 30 minutes and evaporated to dryness, and the residue recrystallised from ethanol to give 345 mg (80%) of rizatriptan benzoate as a white crystalline solid.

M.p. 180-182° C.

IR (KBr): 1605 cm$^{-1}$, 1566 cm$^{-1}$.

$^1$H-NMR (200 MHz, D$_2$O): 2.89 (s, 3H, N(CH$_3$)$_2$), 313 (t, J=7.6 Hz, 2H, CH$_2$CH$_2$N), 3.37 (t, J=7,6 Hz, 2H, CH$_2$CH$_2$N), 5.42 (s, 2H, CH$_2$-benz.), 7.15 (dd, J=1.6 and 8.4 Hz, 1H, ar-indole), 7.31 (s, 1H, ar-indole), 7.48 (m, 4H, ar), 7.59 (s, 1H, ar-indole), 7.90(d, J=8.2 Hz, 1H, ar-benz,), 8.03 (s, 1H, tz), 8.48 (s, 1H, tz).

$^{13}$C-NMR (200 MHz, D$_2$O): 22.9; 45.4; 56.4; 60.3; 111.3; 115.3; 121.0; 125.1; 127.8; 128.6; 129.2; 131.0; 131.6; 134.0; 138.9; 139.0; 146.7; 154.1; 178.4.

13. Process according to claim 1, wherein a Synthesis intermediate of formula (IX):
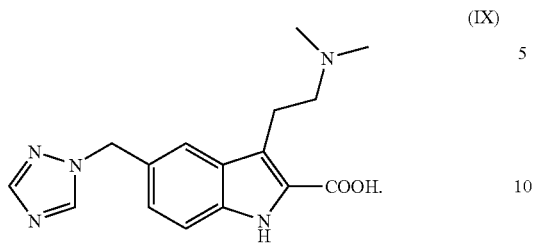

The invention claimed is:

1. Process for preparing a pharmaceutically active compound, rizatriptan, or a pharmaceutically acceptable salt thereof, which comprises the following steps:

a) Preparation of the diazonium salt of the aniline hydrochloride of formula (II)

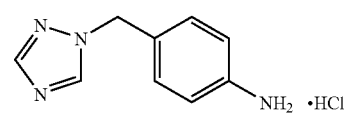

(II)

followed by reduction and acidification to give the hydrazine of formula (III):

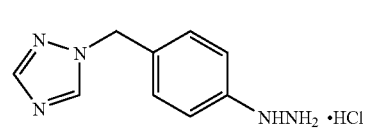

(III)

b) In situ reaction of the hydrazine hydrochloride of formula (III) with α-keto-δ-valerolactone, to give the hydrazone of formula (IV):

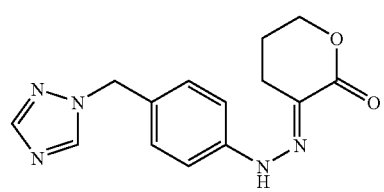

(IV)

c) Fischer indole reaction of the hydrazone of formula (IV), to give the pyranoindolone of formula (V):

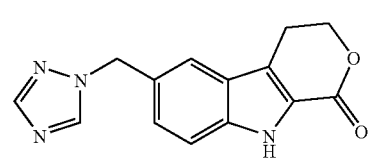

(V)

followed optionally by hydrolysis to give the product of formula (VI):

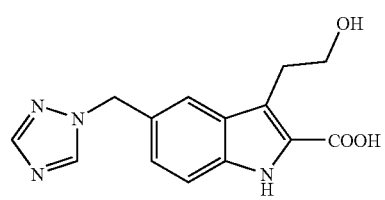

(VI)

d) Transesterification of the compound of formula (V) or esterification of its hydrolysis product of formula (VI), to give a compound of formula (VII):

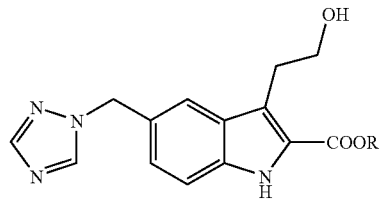

where R represents a straight or branched C1-C4 alkyl chain;

e) conversion of the hydroxyl group of the compound of formula (VII) into dimethylamino, to give the indolecarboxylate of formula (VIII):

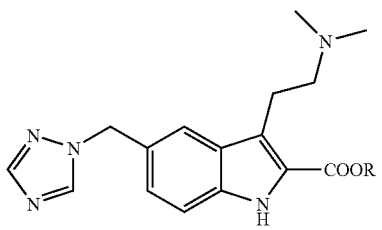

where R has the same meaning as defined above;

f) Saponification of the 2-carboalkoxy group of the compound of formula (VIII), to give the indolecarboxylic acid of formula (IX):

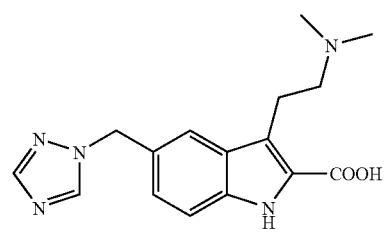

g) Decarboxylation of the indolecarboxylic acid of formula (IX), to give rizatriptan, and eventually, the preparation of a pharmaceutically acceptable salt thereof.

2. Process according to claim 1, wherein in step c) the indolisation is carried out in a solution of dry hydrogen chloride in a straight or branch C1-C4 alcohol chain.

3. Process according to claim 1, wherein steps a), b) and c) are carried out as a one pot reaction.

4. Process according to claim 1, wherein step c) is carried out in aqueous acid medium and is followed by a hydrolysis reaction to give the product of formula (VI).

5. Process according to claim 1, wherein step e) is carried out in two steps:
   e-i) substitution of the hydroxyl group of the compound of formula (VII) by a leaving group X; and
   e-ii) subsequent substitution reaction of the leaving group X with dimethylamine to give the compound of formula (VIII).

6. Process according to claim 5, wherein the leaving group X is selected from a halogen atom, a mesylate group or a tosylate group.

7. Process according to claim 1, wherein step d) is carried out in an alcoholic solution and in the presence of an acid.

8. Process according to claim 1, wherein a Synthesis intermediate of formula (IV):

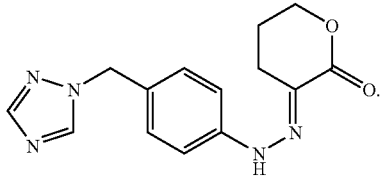

9. Process according to claim 1, wherein a Synthesis intermediate of formula (V):

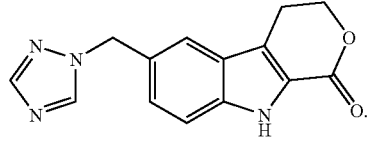

10. Process according to claim 1, wherein a Synthesis intermediate of formula (VI):

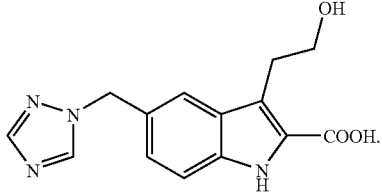

11. Process according to claim 1, wherein a Synthesis intermediate of formula (VII):

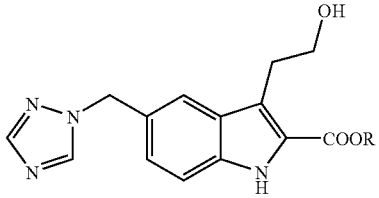

where R represents a straight or branched C1-C4 alkyl chain.

12. Process according to claim 1, wherein a Synthesis intermediate of formula (VIII):

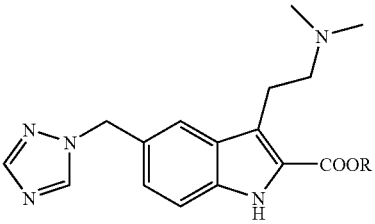

where R represents a straight or branched C1-C4 alkyl chain.